United States Patent
Viner et al.

(10) Patent No.: US 12,276,666 B2
(45) Date of Patent: Apr. 15, 2025

(54) METHOD OF GENERATING AN INCLUSION LIST FOR TARGETED MASS SPECTROMETRIC ANALYSIS

(71) Applicant: Thermo Finnigan LLC, San Jose, CA (US)

(72) Inventors: Roza I. Viner, Fremont, CA (US); Michael A. Blank, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 1940 days.

(21) Appl. No.: 15/875,825

(22) Filed: Jan. 19, 2018

(65) Prior Publication Data

US 2019/0227076 A1 Jul. 25, 2019

(51) Int. Cl.
*G01N 33/68* (2006.01)
*C07K 1/13* (2006.01)
(Continued)

(52) U.S. Cl.
CPC ........ *G01N 33/6848* (2013.01); *C07K 1/13* (2013.01); *C40B 40/10* (2013.01);
(Continued)

(58) Field of Classification Search
None
See application file for complete search history.

(56) References Cited

U.S. PATENT DOCUMENTS

| | | | |
|---|---|---|---|
| 8,227,251 | B2 | 7/2012 | Ranish et al. |
| 8,501,487 | B2 | 8/2013 | Krokhin et al. |

(Continued)

FOREIGN PATENT DOCUMENTS

| | | |
|---|---|---|
| CA | 2799571 A1 | 11/2011 |
| CN | 1692282 A | 11/2005 |

(Continued)

OTHER PUBLICATIONS

Dayon et al., "Relative Quantification of Proteins in Human Cerebrospinal Fluids by MS/MS Using 6-Plex Isobaric Tags," Anal. Chem., 80, 2921-2931, 2008.
(Continued)

*Primary Examiner* — Jennifer Wecker
*Assistant Examiner* — Bryan Kilpatrick
(74) *Attorney, Agent, or Firm* — Klarquist Sparkman, LLP (57) ABSTRACT

A method of generating an inclusion list for targeted mass spectrometric analysis is disclosed. Experimentally-acquired data for a plurality of isobarically-labeled peptides derived by proteolytic digestion of a corresponding protein. The data includes, for each of the isobarically-labeled peptides, a mass-to-charge (m/z) ratio, a charge state, and a chromatographic retention time (RT). The method includes determining a hydrophobicity index (HI) of an unlabeled peptide corresponding to the isobarically-labeled peptide. If the determined HI is less than a threshold value, a substitute unlabeled peptide is selected in accordance with predetermined criteria and predicted properties for the substitute peptide are determined and stored on an inclusion list. If the determined HI for the unlabeled peptide is at least as great as the threshold value, predicted properties for the unlabeled peptide are determined and stored on an inclusion list. The substitute unlabeled peptide may be selected from an available peptide library.

21 Claims, 7 Drawing Sheets

(51) Int. Cl.
  *C40B 40/10* (2006.01)
  *G01N 30/72* (2006.01)
  *G01N 30/86* (2006.01)
  *H01J 49/00* (2006.01)

(52) U.S. Cl.
  CPC ..... *G01N 30/7233* (2013.01); *G01N 30/8679* (2013.01); *G01N 33/6818* (2013.01); *G01N 33/6842* (2013.01); *H01J 49/004* (2013.01); *G01N 2458/15* (2013.01); *H01J 49/0027* (2013.01)

(56) References Cited

U.S. PATENT DOCUMENTS

| | | | |
|---|---|---|---|
| 8,809,772 | B2 | 8/2014 | Bonner et al. |
| 9,048,074 | B2 | 6/2015 | Senko |
| 9,410,966 | B2 | 8/2016 | Bertozzi et al. |
| 9,905,405 | B1 | 2/2018 | Viner et al. |
| 2007/0207555 | A1 | 9/2007 | Guerra et al. |
| 2011/0288779 | A1 | 11/2011 | Satulovsky |
| 2013/0090862 | A1* | 4/2013 | Krokhin ............ G01N 30/72 702/21 |
| 2014/0199716 | A1* | 7/2014 | Bertozzi ............ G01N 33/6848 435/23 |
| 2014/0364337 | A1 | 12/2014 | Hermanson et al. |
| 2015/0153363 | A1 | 6/2015 | Jarvi et al. |

FOREIGN PATENT DOCUMENTS

| | | |
|---|---|---|
| CN | 101611313 A | 12/2009 |
| CN | 105092726 A | 11/2015 |
| EP | 3361258 A1 | 8/2018 |
| WO | WO2014197754 A1 | 12/2014 |

OTHER PUBLICATIONS

Krokhin, "Sequence-Specific Retention Calculator. Algorithm for Peptide Retention Prediction in Ion-Pair RP-HPLC: Application to 300- and 100-A Pore Size C18 Sorbents," Anal. Chem., 78, 7785-7795, 2006.

Legg, "Development and Testing of a Rapid Multiplex Assay for the Identification of Biological Stains," a Dissertation presented to The Faculty of Natural Sciences and Mathematics, University of Denver, 250 pages, 2013.

Rauniyar et al., "Isobaric Labeling-Based Relative Quantification in Shotgun Proteomics," J. Proteome Res., 13, 5293-5309, 2014.

Savitski et al., "Targeted Data Acquisition for ImprovedReproducibility and Robustness of ProteomicMass Spectrometry Assays," J. Am. Soc. Mass, Spectrom., 21, 1668-1679, 2010.

Spicer et al., "3D HPLC-MS with Reversed-Phase Separation Functionality in All Three Dimensions for Large-Scale Bottom-Up Proteomics and Peptide Retention Data Collection," ACS Publications, 9 pages, 2015.

Thermo Scientific Pierce Reagents for Quantitative Proteomics, Protein Quantitation using Mass Spectrometry, 36 pgs., 2014.

GPMAW 9.1 Users Manual Rev. 05-11, 2011, 318 pgs.

Hart-Smith et al., "Improved Quantitative Plant Proteomics via the Combination of Targeted and Untargeted Data Acquisition," Frontiers in Plant Science, vol. 8, Article 1669, Sep. 27, 2017, 16 pgs.

Savitski et al., "Targeted MS for Improved Quantification," J Am Soc Mass Spectrom 2010, 21, 1668-1679.

Zauber and Selbach, "Picky—a simple online method designer for targeted proteomics," Jul. 14, 2017, 13 pgs.

Zolg et al., "Building Proteome Tools Based on a Complete Synthetic Human Proteome," Nature Methods, Received Aug. 5, 2016; accepted Dec. 20, 2016; published online Jan. 30, 2017, 7 pgs.

Hu et al., "GlycoPep MassList: software to generate massive inclusionlists for glycopeptide analyses", Analytical and Bioanalytical Chemistry, vol. 409 (2), 2017, pp. 561-570.

Li et al., "Systematic Comparison of Label-Free, Metabolic Labeling, and Isobaric Chemical Labeling for Quantitative Proteomics on LTQOrbitrap Velos", Journal of Proteome Research, vol. 11 (3), 2012, pp. 1582-1590.

Bailey et al., "Instant spectral assignment for advanced decisiontree-driven mass spectrometry", (Supporting material), Proceedings of the National Academy of Sciences 2012, vol. 109 (22), pp. 1-4.

Bailey et al., "Instant spectral assignment for advanced decisiontree-driven mass spectrometry", Proceedings of the National Academy of Sciences 2012, vol. 109 (22), pp. 8411-8416.

Bailey et al., "Intelligent Data Acquisition Blends Targeted and Discovery Methods," J. Proteome Res., 13, 2152-2161, 2014.

Hu et al., "GlycoPep MassList: software to generate massive inclusion lists for glycopeptide anlayses," Anal. Bioanal. Chem., 409, 561-570, 2017.

* cited by examiner

METHOD OF GENERATING AN INCLUSION LIST FOR TARGETED MASS SPECTROMETRIC ANALYSIS

FIELD OF THE INVENTION

This invention relates to mass spectrometry based quantitation. More specifically, this invention relates to generating an inclusion list for targeted mass spectrometric analysis using results from analysis of corresponding isobarically labeled peptides.

BACKGROUND OF THE INVENTION

Protein quantitation using mass spectrometry requires integration of sample preparation, instrumentation, and software. Strategies to improve sensitivity and comprehensiveness generally require large sample quantities and multidimensional fractionation, which sacrifices throughput. Alternately, efforts to improve the sensitivity and throughput of protein quantification necessarily limit the number of features that can be monitored. For this reason, proteomics research is typically divided into two categories: discovery and targeted proteomics.

Discovery proteomics experiments are intended to identify as many proteins as possible across a broad dynamic range. This often requires depletion of highly abundant proteins, enrichment of relevant fractions, and fractionation to decrease sample complexity.

Quantitative discovery proteomics experiments often utilize isotopic labeling methods, such as labeling with isobaric tags and isotope-coded affinity tags (ICAT) to quantify the proteins. Isobaric tags, which are commercially available in the form of tandem mass tags (TMT) reagents (sold by Thermo Fisher Scientific) and isobaric tags for relative and absolute quantitation (iTRAQ) reagents (sold by AB Sciex), have been repeatedly demonstrated as a facile means of obtaining relative protein quantitation in both small and large scale proteomics studies while providing the powerful capability of simultaneously comparing up to eleven different treatments, time points, or samples. These protein labeling strategies incorporate isotopes into proteins and peptides, resulting in distinct mass shifts but otherwise identical (among peptides labeled with different isotopomers of a reagent set) chemical properties. This allows several samples to be labeled and combined prior to processing and liquid chromatography-tandem mass spectrometry (LC-MS/MS) analysis. This multiplexing reduces sample processing variability, improves specificity by quantifying the proteins from each condition simultaneously, and requires less liquid chromatography-mass spectrometry (LC-MS) and data analysis time.

While there is some cost associated with the mass tagging kits, tens of thousands of proteins can be identified and quantified across multiple samples (representing, for example, different disease states) in a highly efficient multiplexed fashion with a single LCMS experiment. Numerous high importance and significantly regulated protein targets of interest often emerge from these studies and become the subject of future routine analyses using highly sensitive and robust targeted techniques, without the added expense or steps of isobaric labeling.

Targeted proteomics experiments are typically designed to quantify less than one hundred proteins with very high precision, sensitivity, specificity and throughput. Targeted MS quantitation strategies use specialized workflows and instruments to improve the specificity and quantification of a limited number of features across hundreds or thousands of samples. These methods typically minimize the amount of sample preparation to improve precision and throughput.

Targeted quantitative proteomic workflows typically involve protein denaturation, reduction, alkylation, digestion and desalting prior to LC-MS/MS analysis on a mass spectrometer instrument capable of quantifying peptides by monitoring specific mass windows for peptides of interest, fragmenting the isolated peptide(s), and then quantifying several fragment ions that are specific for the peptide of interest. This acquisition strategy, of which selective reaction monitoring (SRM) is a common example, together with chromatographic retention time information, provides very high sensitivity, specificity, dynamic range and throughput.

Unfortunately, current workflows suffer from a severe disconnection between isobarically labeled discovery quantitation and routine targeted label-free quantitation of significant peptides. As the isobaric labeling alters not only the mass of the peptide but also its charge, ionization efficiency, and hydrophobicity, targeting a highly regulated peptide from an isobaric experiment is not straightforward. Yet, scheduling of analytes using their retention time is important for reproducible quantitation when the list of targeted peptides grows long. This often necessitates an intermediate validation step using a label-free quantitative technique such as data independent acquisition (DIA) or MS1 based discovery quantitation which can be costly in terms of performance, sample, instrument time, and reagents. While it is possible to use label-free discovery proteomics and then directly transition to targeted routine quantitation of key peptides, multiple serial analyses must be performed to deliver the same information acquired in a single multiplexed isobaric labeling experiment.

What is needed is a method and system for translating directly from multiplexed isobaric labeling discovery quantitation to routine label-free targeted quantitation without an intermediate validation step.

SUMMARY

Methods and systems are disclosed herein for translating the results of an isobaric labeling experiment into an inclusion list for targeted mass spectrometric quantitation. In accordance with one embodiment of the present invention, a method of generating an inclusion list for targeted mass spectrometric analysis is disclosed. The method includes receiving, at a data processing system, experimentally-acquired data for a plurality of isobarically-labeled peptides wherein each of the isobarically-labeled peptides is derived by proteolytic digestion of a corresponding protein. The data includes, for each one of the isobarically-labeled peptides, a mass-to-charge ratio (m/z), a charge state, and a chromatographic retention time. The following steps are performed, via a data processing system, for each one of the isobarically-labeled peptides: determining a hydrophobicity index (HI) of an unlabeled peptide corresponding to the isobarically-labeled peptide; if the determined HI is less than a threshold value, selecting a substitute unlabeled peptide in accordance with predetermined criteria, the substitute unlabeled peptide being derivable by proteolytic digestion of the protein from which the isobarically-labeled peptide is derived, determining and storing on the inclusion list predicted properties for the substitute unlabeled peptide, the predicted properties including a predicted m/z, a predicted charge state, and a predicted chromatographic retention time, wherein the predicted chromatographic retention time is based on an HI of the substitute unlabeled peptide and chromatographic conditions for the targeted analysis; if the determined HI for the unlabeled peptide is at least as great as the threshold value, determining and storing on the inclusion list predicted properties for the unlabeled peptide, the predicted properties including a predicted m/z, a predicted charge state, and a predicted chromatographic retention time, wherein the predicted chromatographic retention time is based on the determined HI of the unlabeled peptide and chromatographic conditions for the targeted analysis.

In some embodiments, the predetermined criteria include the substitute unlabeled peptide having an HI of 2.0% acetonitrile (ACN) or greater at LC gradient initial conditions. In some embodiments, the threshold value of the unlabeled peptide is 1.0% ACN at LC gradient initial conditions. The LC gradient initial (i.e., starting) condition refers to the beginning of a chromatographic gradient before a specific peptide elutes from the LC and is injected into the mass spectrometer. In some embodiments, the HI is at least 1% ACN at the LC gradient initial conditions. The substitute unlabeled peptide may be selected from a stored library comprising proteins and corresponding sets of proteotypic peptides having known HI values. In some embodiments, the proteolytic digestion comprises tryptic digestion.

In one embodiment, the predicted properties further include a predicted fragment ion m/z.

The experimentally-acquired data may also include an amino acid sequence of each peptide.

In one embodiment, the predicted chromatographic retention time for the corresponding unlabeled peptide is determined further based on its relation to an experimentally-acquired chromatographic retention time of a reference peptide. The reference peptide can be, but is not limited to, at least one peptide of a peptide retention time calibration (PRTC) mixture.

The isobarically-labeled peptides can be, but are not limited to, tandem mass tag (TMT)-labeled peptides, isobaric tags for relative and absolute quantitation (iTRAQ)-labeled peptides, Combinatorial Isobaric Mass Tags (CMTs), or N,N-Dimethylated Leucine (DiLeu) isobaric tags.

In one embodiment, the targeted mass spectrometric analysis comprises $MS^n$ quantitation. The $MS^3$ quantitation can be, but is not limited to, parallel reaction monitoring (PRM), selected reaction monitoring (SRM) or synchronous precursor selection (SPS).

In one embodiment, the hydrophobicity index of the corresponding unlabeled peptide is calculated using a retention time prediction tool. The retention time prediction tool may be a sequence-specific retention time calculation tool such as SSRCalc.

In another embodiment of the present invention, a method of generating an inclusion list for targeted mass spectrometric analysis is provided. The method includes receiving, at a data processing system, experimentally-acquired data for a plurality of isobarically-labeled peptides wherein each of the isobarically-labeled peptides is derived by proteolytic digestion of a corresponding protein. The data includes, for each one of the isobarically-labeled peptides, a mass-to-charge ratio (m/z), a charge state, and a chromatographic retention time. The following steps are performed, via a data processing system, for each one of the isobarically-labeled peptides: determining a hydrophobicity index (HI) of an unlabeled peptide corresponding to the isobarically-labeled peptide; if the determined HI is less than a threshold value, selecting a substitute unlabeled peptide in accordance with predetermined criteria, the substitute unlabeled peptide being derivable by proteolytic digestion of the protein from which the isobarically-labeled peptide is derived, determining and storing on the inclusion list predicted properties for the substitute unlabeled peptide, the predicted properties including a predicted m/z, a predicted charge state, a predicted fragment ion m/z, and a predicted chromatographic retention time, wherein the predicted chromatographic retention time is based on an HI of the substitute unlabeled peptide, chromatographic conditions for the targeted analysis, and on its relation to an experimentally-acquired chromatographic retention time of a reference peptide; if the determined HI for the unlabeled peptide is at least as great as the threshold value, determining and storing on the inclusion list predicted properties for the unlabeled peptide, the predicted properties including a predicted m/z, a predicted charge state, a predicted fragment m/z, and a predicted chromatographic retention time, wherein the predicted chromatographic retention time is based on the determined HI of the unlabeled peptide, chromatographic conditions for the targeted analysis, and on its relation to an experimentally-acquired chromatographic retention time of a reference peptide.

DETAILED DESCRIPTION OF EMBODIMENTS

Embodiments of the present invention are directed to systems and methods of translating the results of an isobaric labeling experiment directly into an inclusion list for label-free targeted mass spectrometric analysis or quantitation. The methods described herein may be executed in a data processing system, alternatively referred to as a computer. Generally described, the data processing system may comprise one or a combination of devices, including but not limited to general-purpose and specialized processors and application-specific circuitry, having logic (e.g., in the form of software code) configured to perform the steps of the methods. The data processing system will also typically include local or network storage for holding input and output data, as well as a display or other device for presenting results to the instrument operator. The storage may also hold the peptide library described below in further detail.

As used herein, the term "retention time" refers to the time elapsed from when a sample is first introduced into a chromatography column and is eluted from the chromatography column.

Figure 1:
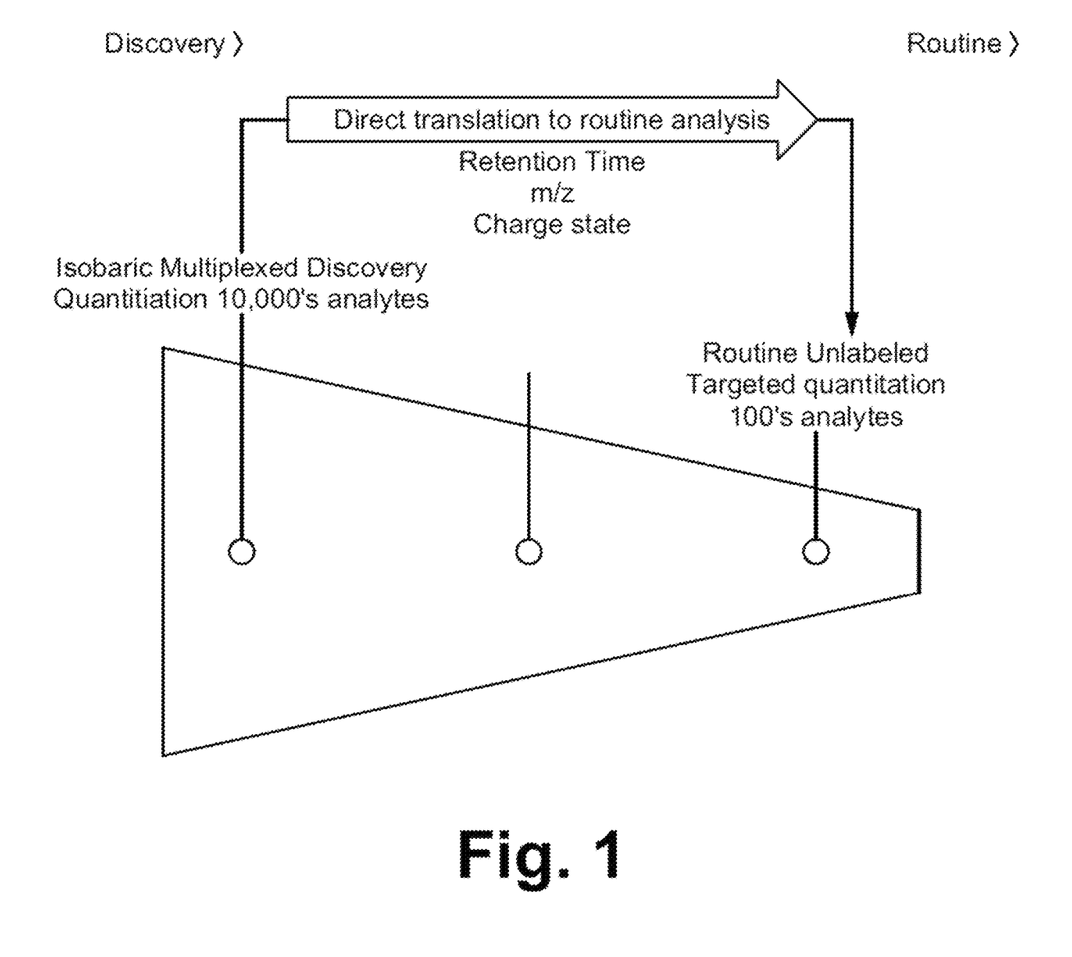
FIG. 1 shows a broad overview of the process for generating an inclusion list for targeted mass spectrometric analysis, in accordance with one embodiment of the present invention.

FIG. 1 shows a broad overview of the process for generating an inclusion list for targeted mass spectrometric analysis, in accordance with one embodiment of the present invention. The first step involves receiving data generated in an isobaric multiplexed discovery quantitation study. Generally described, isobaric multiplexed discovery quantitation experiments involve separately preparing a number of samples, enzymatically digesting the samples to produce cleaved peptides, adding a different reagent from an isobaric labeling reagent set to each one of the samples to label the peptides contained therein, combining the labeled sample, and then analyzing the combined sample by tandem or MSn mass spectrometry. Fragmentation of the co-eluting labeled peptides yields characteristic low-mass reporter ions, with each reporter ion species corresponding to a different one of the combined samples. The reporter ion intensities in the product ion spectra may be used to determine the relative amounts of specific peptides in the samples. In one illustrative example, the samples include a first group of samples extracted from biological tissue or fluids of diseased animals/humans, and a second of samples extracted from biological tissue or fluids of healthy (control) animals/humans, and the experiment is intended to identify peptides that are differentially expressed (i.e., present in higher or lower amounts) in one group relative to another; the identified peptides may be further investigated as biomarker candidates. The spectral data generated by the mass spectrometer is processed by data analysis software (e.g., Proteome Discoverer software from Thermo Fisher Scientific) to provide a list of labeled peptides identified in the samples, and the relative amounts of the labeled peptides across the individual samples. The list will further include, for each labeled peptide, the retention time, precursor ion mass-to-charge ratio (m/z) and charge state. This list may be processed in an automated, semi-automated, or fully manual fashion to select a set of peptides of interest (e.g., those showing a high degree of differentiation between disease and control group samples), derived by proteolytic digestion of a corresponding protein, for label-free targeted analysis.

It should be recognized that while the foregoing example describes labeling peptides produced by proteolytic digestion, other implementations may forego digestion and instead utilize labeling of intact proteins contained in the sample.

The peptide list derived by performing a multiplexed discovery quantitation experiment and selecting peptides of interest from the results, as described above, includes properties (retention time, m/z, charge state) measured for the labeled versions of the peptides of interest, i.e., the peptide bonded to a labeling moiety. In order to set up a targeted quantitation experiment to measure label-free peptides, the properties for the label-free versions of the peptides of interest need to be determined. Embodiments of the present invention obviate the need for an intermediate validation step using a label-free quantitative technique such as DIA or MS1 based discovery quantitation, which can be costly in terms of performance, sample, instrument time, and reagents, and permits direct translation from multiplexed discovery quantitation to routine label-free targeted quantitation.

Figure 2:
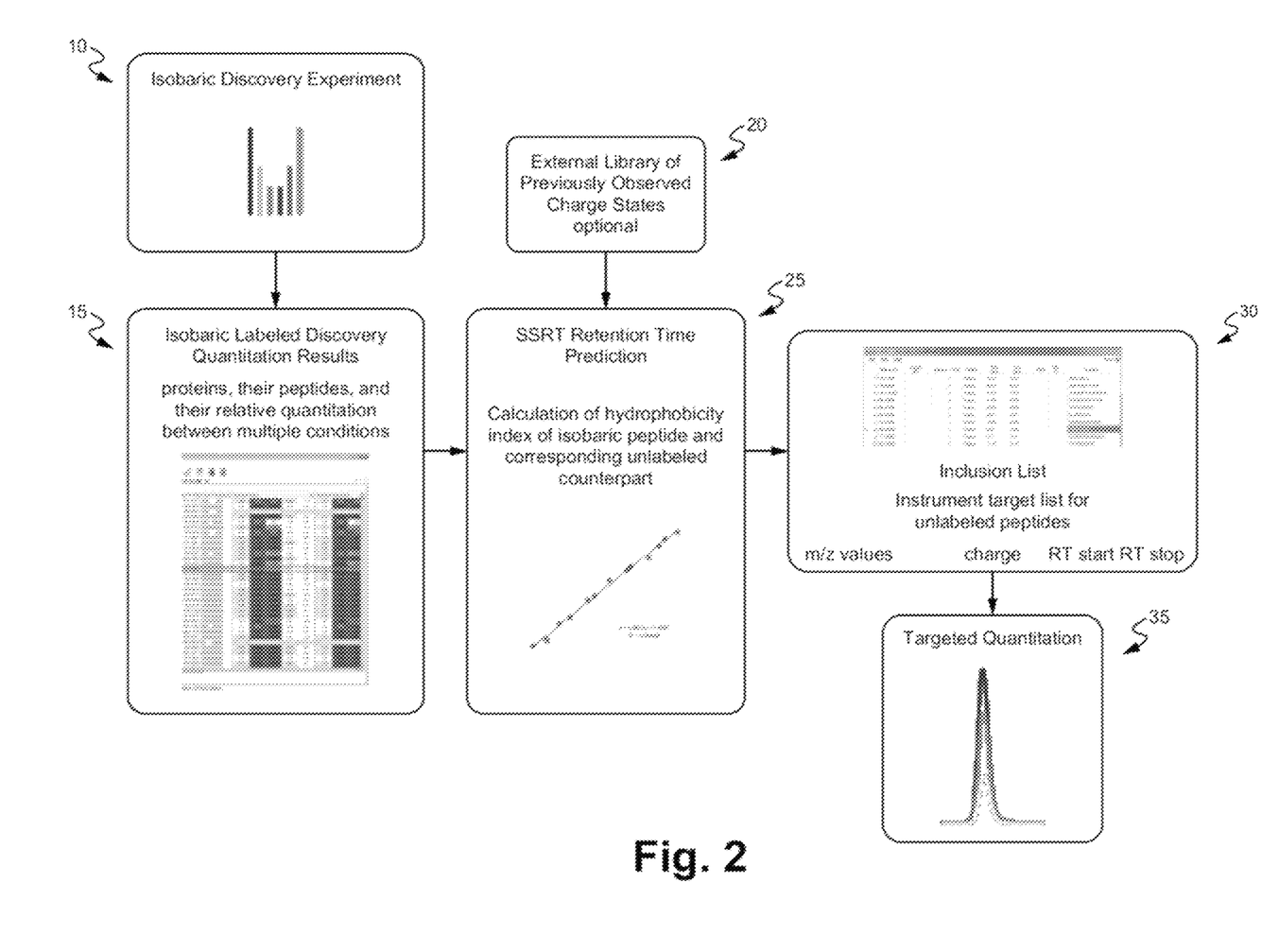
FIG. 2 is a diagram illustrating the workflow involved in generating an inclusion list for targeted mass spectrometric analysis, in accordance with one embodiment of the present invention.

FIG. 2 is a diagram illustrating the workflow involved in generating an inclusion list for targeted mass spectrometric analysis, in accordance with one embodiment of the present invention. A multiplexed discovery experiment 10 using isobarically-labeled samples outputs the isobarically-labeled discovery quantitation results 15. These results comprise but are not limited to a list of identified peptides derived by proteolytic digestion of a corresponding protein and corresponding properties (m/z values, charge states, and retention times) determined for the labeled version of the peptides which, in the manned discussed below, may be used to calculate properties to be used for label-free targeted quantitation.

When performing a targeted experiment to quantify label-free peptides, it is highly advantageous to reliably predict retention times for the target analytes, such that the instrument may be operated to monitor only those analytes that are expected to elute from the chromatographic column at specific points in chromatographic time. This practice avoids wasting instrument time caused by monitoring transitions corresponding to analytes whose presence would not be expected.

The hydrophobicity index, a semi-empirical metric, is one type of retention-time prediction index. A value of the hydrophobicity index may be calculated for each peptide based on the peptide m/z, charge state, and chromatographic retention time. Peptide retention times that are observed in reverse-phase high pressure liquid chromatograph are found to depend on peptide hydrophobicity and can be modeled in terms of the hydrophobicity index.

In one embodiment, a hydrophobicity index for each identified and quantified peptide sequence of interest may be calculated using a sequence-specific retention time calculator tool that estimates retention times from the amino acid composition and sequence of a peptide (e.g., the SSRCalc algorithm described in Krokhin, "Sequence-Specific Retention Calculator. Algorithm for Peptide Retention Prediction in Ion-Pair RP-HPLC: Application to 300- and 100-A Pore Size C18 Sorbents, Analytical Chemistry, Vol. 78, No. 22, pp. 7785-95 (2006), which is incorporated herein by reference). An optional external library 20 containing only previously observed charge states for transitions or fragments of these peptides can also be used for determining their predicted retention times 25 but is not required. An inclusion list 30 with peptide parent m/z, charge state, and retention time is supplied to run a targeted quantitation experiment 35.

As noted above, the inclusion list is a compilation or listing of one or more peptides derived by proteolytic digestion, m/z values, charge states, and retention times which have been identified and selected for MS/MS or MS" analysis. In a MS" scan, specific ions detected in a survey scan are selected to enter a collision chamber. The ability to define the ions—by the inclusion list—for MS" allows data to be acquired for specific precursors. The series of fragments that is generated in the collision chamber is then analyzed again by mass spectrometry, and the resulting spectrum is recorded and may be used to identify the amino acid sequence of the particular peptide. This sequence, together with other information such as the peptide mass, may then be used to identify the protein. The ions subjected to MS" cycles may be user defined or determined automatically by the spectrometer.

Figure 3A:
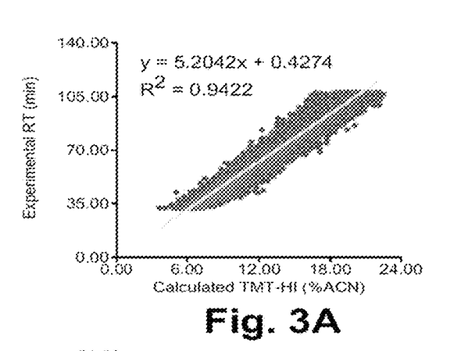
FIGS. 3A-3C are a series of graphs showing a method of generating an inclusion list for targeted mass spectrometric analysis, in accordance with one embodiment of the present invention.
Figure 3B:
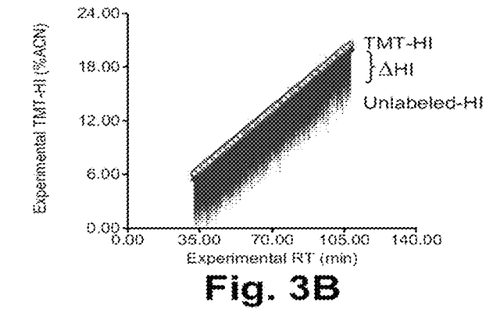
Figure 3C:
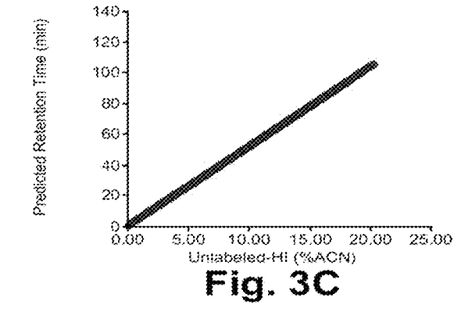

FIGS. 3A-3C are a series of graphs showing a method of generating an inclusion list for targeted mass spectrometric analysis, in accordance with one embodiment of the present invention.

FIG. 3A is a graph showing the experimental retention time vs. hydrophobicity indices (HIs) for isobarically labeled peptides. The HIs for the isobarically labeled peptides—TMT labeled peptides, in this example—were determined by using an equation for linearization of the HI of the TMT labeled peptides and their retention times. In one embodiment, the equation for the linear fit or linearization of the HI is provided on the upper left section of FIG. 3A.

FIG. 3B is a graph showing the experimental HI values vs. experimental retention times for the isobarically labeled peptides. The experimental HI values for the isobarically labeled peptides ("TMT-HI") were calculated using the equation in FIG. 3A for linearization. The "ΔHI" is the individually adjusted HI index for each TMT labeled peptide which yields an HI index for the unlabeled counterpart peptides ("Unlabeled-HI").

Isobaric labeling (e.g. TMT labeling) alters not only the mass of the peptide but also its charge and hydrophobicity. It has been discovered, however, that some of the unlabeled peptides derived by proteolytic digestion of a corresponding protein cannot be readily analyzed by the liquid chromatography-mass spectrometry (LCMS) technique, as the unlabeled peptides may be too hydrophilic to be retained in a chromatography column. For these peptides, conversion from an isobarically-labeled peptide yields a corresponding unlabeled peptide possessing negative or close to zero HI values, and thus the unlabeled peptide cannot be analyzed in a targeted LCMS method. For example, for a TMT labeled peptide SSAAPPPPPR, the HI is 1.94% ACN and the RT is 12.24 minutes. But the same peptide without the TMT label has a calculated HI of less than 1% ACN. As a result, the peptide would elute in the loading step of a chromatographic run and hence its retention time could not be predicted, rendering it impossible to perform targeted LCMS analysis of this peptide.

To overcome this limitation, if the determined HI of the unlabeled counterpart peptide (corresponding to the isobarically-labeled peptide) is less than a threshold value, a substitute unlabeled peptide, belonging to the same protein, is selected in accordance with predetermined criteria. The substitute unlabeled peptide is an alternative proteotypic peptide derivable by proteolytic digestion of the protein from which the isobarically-labeled peptide was derived. In an illustrative embodiment, the substitute unlabeled peptide is automatically selected from a library, stored in the data processing system, which contains, for each of a plurality of proteins, a list of corresponding proteotypic peptides as well as the HI value for each proteotypic peptide (or, alternatively, information about the peptide, such as its amino acid sequence, from which its HI value may be calculated). The library may include additional information for each proteotypic peptide, such as predicted charge states and m/z's of its pseudo-molecular ions as well as predicted charge states and m/z's of product ions formed by fragmentation of the pseudo-molecular ions. In the event that it is determined that the HI value of the unlabeled counterpart peptide is below a threshold and is thus not suitable for analysis by LCMS, the library is searched to identify one or more substitute unlabeled peptide candidates corresponding to the protein from which the unlabeled counterpart was derived. Predetermined criteria are applied to the one or more identified substitute unlabeled peptide candidates to select the substitute unlabeled peptide to be used for the targeted analysis. The criteria will include a minimum HI value (i.e., an HI that is sufficiently great such that the substitute unlabeled peptide will absorb to the column media and not be eluted during loading). The criteria applied for selection may also be based on the m/z's of the pseudo-molecular ion and/or its products (to ensure that they are detectable by the mass analyzer, or that they are not obscured by interfering co-eluting ion species), and the predicted abundances of the pseudo-molecular ion and/or its products (to screen out candidate substitute unlabeled ion species that will not yield peaks of sufficient signal-to-noise ratio to be confidently identified or quantified. The step of selection of the substitute unlabeled peptide may be performed in a fully automatic fashion, i.e., without any user intervention. Alternatively, certain implementations of the method may employ a semi-automated routine, whereby the data processing system identifies a plurality of candidates that may be used as the substitute unlabeled peptide and presents that list to the user, and the user them manually selects the substitute unlabeled peptide to be utilized for targeted analysis from the list.

In one embodiment, the threshold value for the determined HI of the unlabeled counterpart is 1.0% ACN or less at LC gradient initial conditions. In one embodiment, the predetermined criteria used to select an unlabeled peptide is an HI greater than at least 2.0% ACN at LC gradient initial conditions.

FIG. 3C is a graph of the predicted retention time vs. HI for the unlabeled peptides. The predicted retention time for the unlabeled peptides were calculated using the equation for linearization as previously determined in FIG. 3A.

In an exemplary application of the methodology described in connection with FIGS. 3A-3C, a TMT-labeled peptide (or other suitably labeled peptide) identified from the discovery quantitation MS data and having determined to be of interest, such as IVAVTGAEAQK because of its relative quantitation values, is selected for subsequent targeted quantitation.

First, the intact mass of the corresponding unlabeled peptide is calculated from its sequence (IVAVTGAEAQK). The molecular weight of each amino acid (I, V, A, V, T, G, A, E, A, Q, K) in the sequence can be found in any chemical table. The sum of the molecular weights of n amino acids, minus n–1 water molecules, adds up to the intact mass of the unlabeled peptide. Next, the charge state(s) of the unlabeled form of the peptide is (are) predicted based on its sequence or provided by referencing an external database or library such as NIST/EPA/NIH Mass Spectral Library, a peptide repository such as PeptideAtlas, which may be accessed at http://www.peptideatlas.org, or by tools like SSRCalc (http://hs2.proteome.ca/SSRCalc/SSRCalc.html). With the intact mass and expected charge state value, an m/z value for the unlabeled peptide can be readily computed.

Subsequently, using the retention time prediction outlined in FIGS. 3A-3C, a predicted retention time for the unlabeled version of the peptide can be determined. Briefly, the observed retention times for all TMT-labeled peptides identified in the discovery quantitation experiment are plotted against their calculated hydrophobicity index (HI) values (expressed as % ACN). As shown in FIG. 3A, these values are linearized and then adjusted to give the HI values of the unlabeled counterpart peptides which are less than those of the labeled (TMT) peptides, as seen in FIG. 3B. From these HI values (expressed in % ACN) for the unlabeled peptides their retention times on a given gradient can be predicted. In FIG. 3C, these values are linearized using the same equation as for the TMT-labeled peptides determined previously to give the predicted retention time on the same gradient. Together with the m/z value and charge state, there is significant information to build a targeted inclusion list to quantify these peptides by techniques such as PRM.

Figure 5:
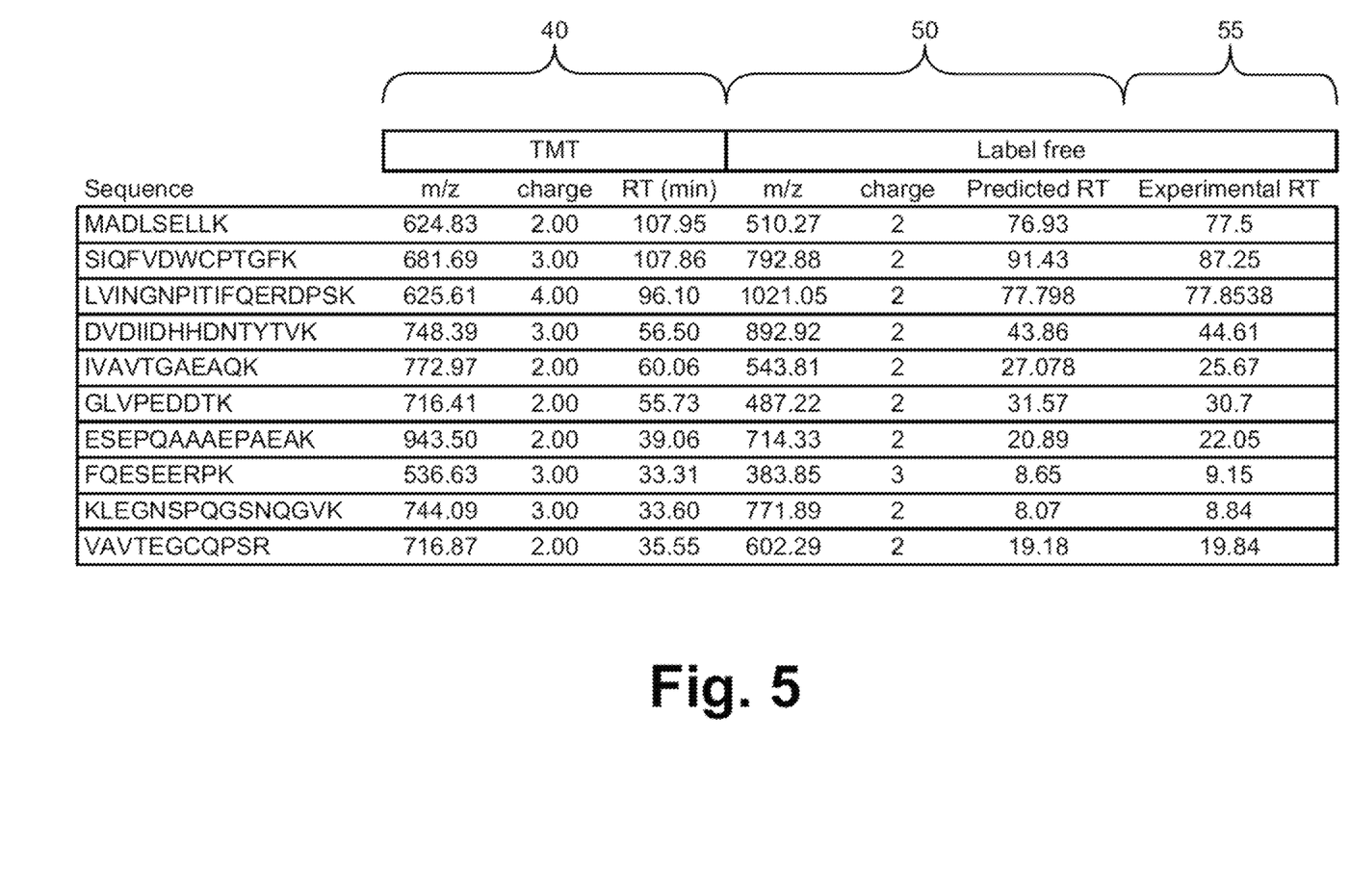
FIG. 5 shows the data for generating an inclusion list, beginning with the quantitative results of TMT-labeled peptides of interest to a list of corresponding label-free predicted properties. The experimental retention times for the label-free peptides are shown on the right-most column of the table.

By way of example using the equation for linearization of the HI of the TMT labeled peptides (y=5.2042x+0.4274) and experimental retention time for the TMT-labeled sequence in FIG. 5, in one embodiment of the present invention, the HI-labeled for IVAVTGAEAQK is calculated to be approximately 11.45% ACN. From FIG. 3B, the empirically adjusted HI for the labeled HI is adjusted to give the HI for the unlabeled counterpart peptide which is approximately 5.1210% ACN. Applying the empirically derived linearized equation above for the gradient from the TMP experiment empirically derived TMT: y=5.2042x+0.4274, where y is the predicted retention time (in minutes), x=HI % ACN of the unlabeled peptide, 5.2042 is the slope (retention time empirical/% ACN) and 0.4274 is the delay (in minutes), the predicted retention time=5.2042 (5.1210)+0.4274, which is equal to approximately 27.078.

The following illustrates another example of the present invention for predicting the retention time where the TMT linearized equation is not used when the gradient is different. In this example, the gradient time is 60 minutes (Δy=60 minutes), and the initial and final concentrations of ACN are 1 and 31%, respectively (i.e., Δx=30% ACN). The slope=Δy/Δx=60 minutes/30% ACN=2 minutes/% ACN. Using the general equation y=mx+b, where y is the predicted retention time, m is the slope or intercept, x is the HI value for the unlabeled peptide, and b is, in this example, 0.5 minutes for the delay or adjustment in minutes, the predicted retention time (y)=(2 minutes/% ACN)*5.1210% ACN+0.5 minutes, which is approximately 10.74 minutes.

In the example of IVAVTGAEAQK, the charge state is predicted to be +2 for the unlabeled peptide, in this case equal to the TMT-labeled counterpart, such that the m/z value for the unlabeled peptide reflects only the mass difference of the TMT label on the N-terminus and lysine. In contrast, a dramatic change in retention time of approximately 35 minutes is predicted for the unlabeled peptide, and the observed retention time (for the unlabeled peptide in label-free experiments) is within 90 seconds of this prediction, as shown in the sequence data of FIG. 5.

It is also important to supply information about the solvent system (e.g., ACN, methanol, water, or an ion pairing agent such as TFA or FA), specifically mobile phase composition to ensure accurate HI calculations.

In another exemplary application of the methodology described in connection with FIGS. 3A-3C, a TMT-labeled peptide (or other suitably labeled peptide), AQHEDQVEQYKK, identified from the discovery quantitation MS data and having determined to be of interest because of its relative quantitation values, is selected for subsequent targeted quantitation. The AQHEDQVEQYKK peptide was derived by proteolytic digestion of the LAMIN A/C protein.

First, the intact mass of the corresponding unlabeled peptide is calculated from its sequence (AQHEDQVEQYKK). The molecular weight of each amino acid (A, Q, H, E, D, Q, V, E, Q, Y, K, K) in the sequence can be found in any chemical table. The sum of the molecular weights of n amino acids, minus n−1 water molecules, adds up to the intact mass of the unlabeled peptide. Next, the charge state(s) of the unlabeled form of the peptide is (are) predicted based on its sequence or provided by referencing an external database or library such as NIST/EPA/NIH Mass Spectral Library, a peptide repository such as PeptideAtlas, which may be accessed at http://www.peptideatlas.org, or by tools like SSRCalc (http://hs2.proteome.ca/SSRCalc/SSR-Calc.html). With the intact mass and expected charge state value, an m/z value for the unlabeled peptide can be readily computed. It should be noted that other databases, libraries, and tools may be accessed or utilized to identify charge states associated with the peptides.

Figure 6:
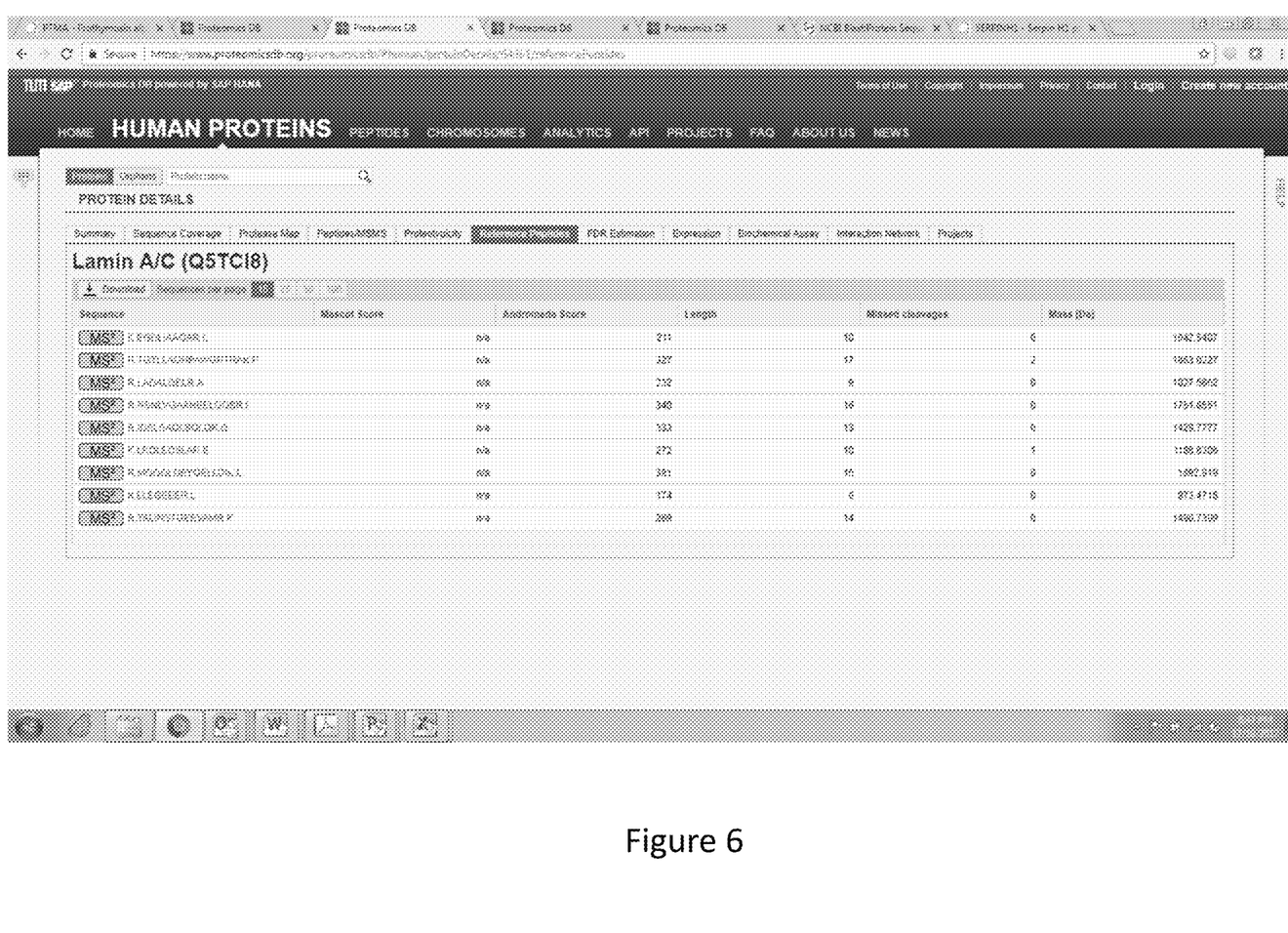
FIG. 6 is a screen capture of a table containing information including a list of peptide sequences for a particular protein from the Proteomics DB library.

Subsequently, using the retention time prediction outlined in FIGS. 3A-3C, a predicted retention time for the unlabeled version of the peptide can be determined. Briefly, the observed retention times for all TMT-labeled peptides identified in the discovery quantitation experiment are plotted against their calculated hydrophobicity index (HI) values (expressed as % ACN). As shown in FIG. 3A, these values are linearized and then adjusted to give the HI values of the unlabeled counterpart peptides which are less than those of the labeled (TMT) peptides, as seen in FIG. 3B. From these HI values (expressed in % ACN) for the unlabeled peptides their retention times on a given gradient can be predicted. The HI for the peptide sequence AQHEDQVEQYKK without the TMT label, however, has a predicted unlabeled HI of 0.95% ACN with a corresponding unlabeled retention time of approximately 5.4 minutes. As such, the AQHEDQVEQYKK peptide would elute in the loading step and thus could not be observed. To overcome this problem, an available peptide library such as the Proteome Tools library (accessible via the proteometools.org website) is searched to replace the AQHEDQVEQYKK peptide with a peptide having an HI value of at least 1.0 or higher and derived from the same Lamin A/C protein. In one example, as shown in the screen capture of FIG. 6 showing a table from the Proteomics DB library, peptide sequence EGDLIAAQAR may be substituted for peptide sequence AQHEDQVEQYKK and used in its place for subsequent label-free quantitation of the Lamin A/C protein. The peptide sequence EGDLIAAQAR has a TMT-labeled HI of 9% ACN and an unlabeled HI of 4.86% ACN, with a predicted retention time of approximately 25.5 minutes. Some consideration may be given to selecting substitute peptides whose retention times are not coincidental with other peptides already present on the nascent targeted inclusion list.

In FIG. 3C, these values are linearized using the same equation as for the TMT-labeled peptides determined previously to give the predicted retention time on the same gradient. Together with the m/z value and charge state, there is significant information to build a targeted inclusion list to quantify these peptides by techniques such as PRM.

Figure 4A:
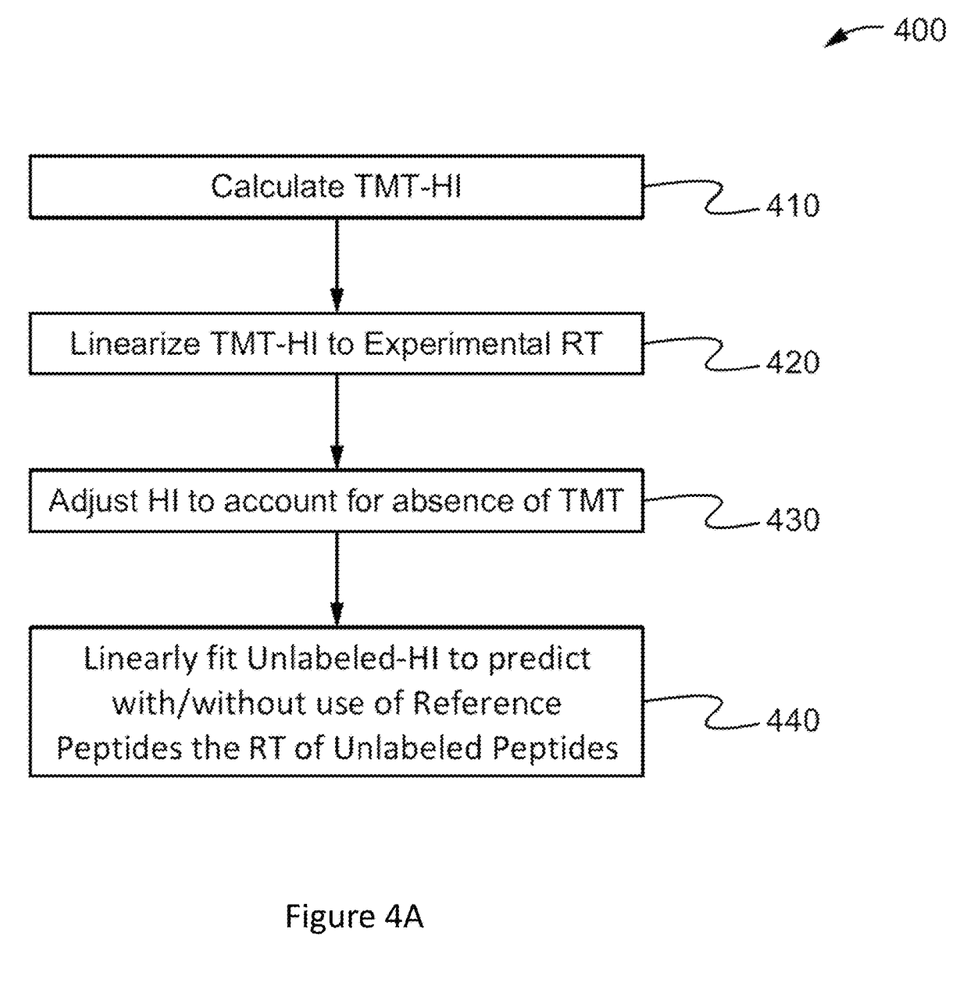
FIG. 4A is a flowchart illustrating a method of generating an inclusion list for targeted mass spectrometric analysis, in accordance with one embodiment of the present invention.

FIG. 4A is a flowchart 400 illustrating the method of generating an inclusion list for targeted mass spectrometric analysis, which was shown in the graphs of FIGS. 3A-3C, in accordance with one embodiment of the present invention. In step 410, the HIs for the TMT labeled peptides are calculated and, in step 420, are linearized by applying a linear fit to experimentally-acquired retention times. In step 430, the HIs for the TMT labeled peptides are adjusted to account for the absence of the TMT labeling. In other words, the HI index for each TMT labeled peptide is individually adjusted to yield HIs for the corresponding unlabeled counterpart peptides. In step 440, retention times for the corresponding unlabeled peptides are predicted using the equation for linear fit as previously determined. As a result, these retention times are independent of gradient length, depending only on HI and solvent composition. To further accommodate potentially different chromatographic conditions between the labeled and unlabeled experiments, reference peptides (e.g., PRTC) can be employed as retention time landmarks to refine predicted retention times for disparate gradients.

Figure 4B:
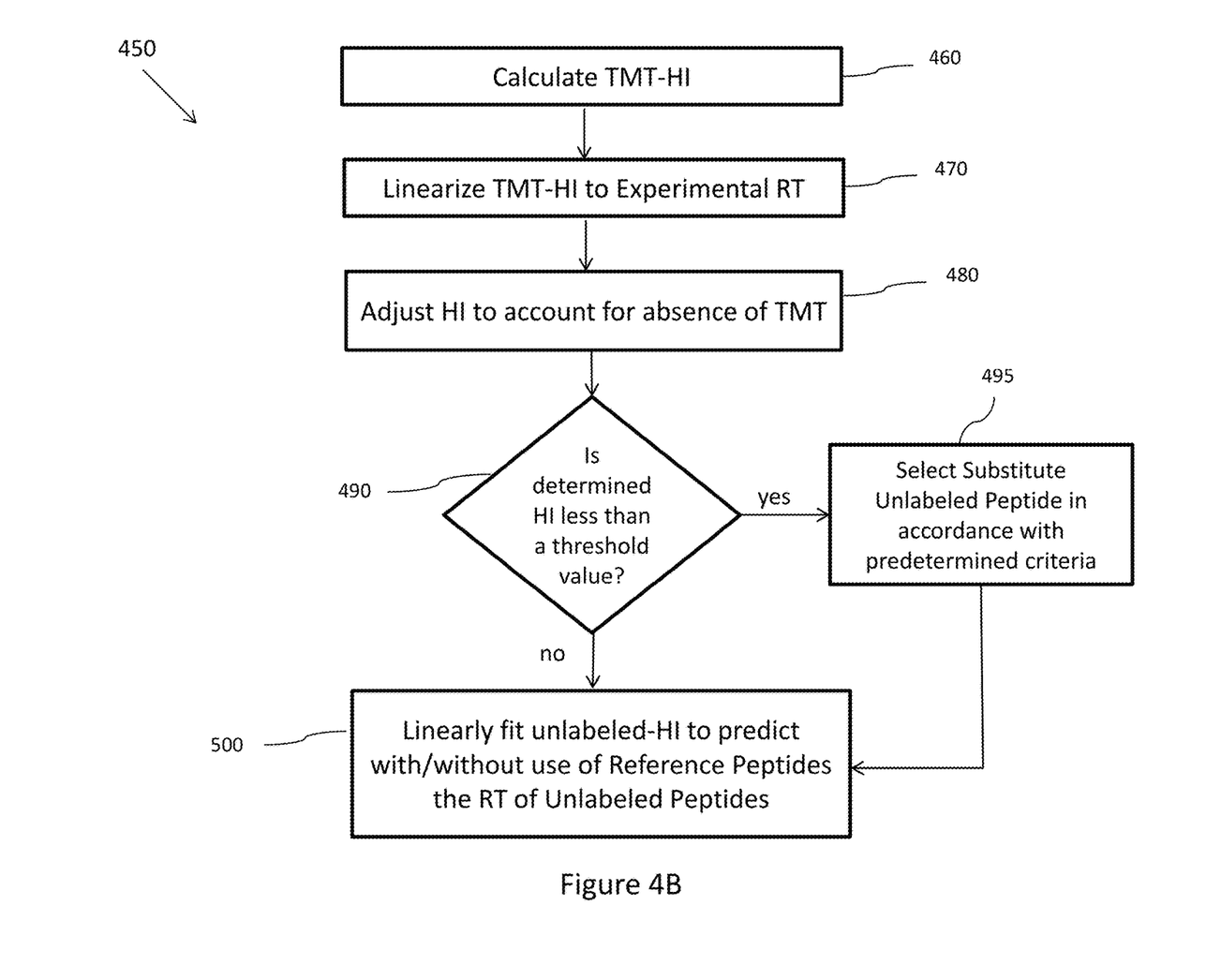
FIG. 4B is a flowchart illustrating a method of generating an inclusion list for targeted mass spectrometric analysis, in accordance with an alternative embodiment of the present invention.

FIG. 4B is another flowchart 450 illustrating a method of generating an inclusion list for targeted mass spectrometric analysis, in accordance with an alternative embodiment of the present invention. In step 460, the HIs for the TMT labeled peptides are calculated and, in step 470, are linearized by applying a linear fit to experimentally-acquired retention times. In step 480, the HIs for the TMT labeled peptides are adjusted to account for the absence of the TMT labeling. In other words, the HI index for each TMT labeled peptide is individually adjusted to yield HIs for the corresponding unlabeled counterpart peptides. Thereafter, the method proceeds to step 490, where the data processing system compares the determined HI of the unlabeled peptide to a threshold value. If the determined HI is less than a threshold value, a substitute unlabeled peptide is selected, in step 495, in accordance with predetermined criteria. In some embodiments, the threshold value of the unlabeled HI is 1.0 and the predetermined criteria is a substitute unlabeled peptide having an HI greater than at least 2.0, both at LC gradient initial conditions. As an example, if the determined HI is 0.5, any substitute unlabeled peptide from the same parent protein (from which the isobarically-labeled peptide was derived by proteolytic digestion) having an HI greater than at least 2.0 may be selected and used in its place for subsequent label-free quantitation of the parent protein via step 500, where retention times for the corresponding unlabeled peptides are predicted using the equation for linear fit as previously determined. Some consideration may be given to selecting substitute peptides whose retention times are not coincidental with other peptides already present on the nascent targeted inclusion list.

If, at step 490, the determined HI for the unlabeled peptide is at least as great as the threshold value, predicted properties for the unlabeled peptide, in step 500, are determined and stored on the inclusion list. In this instance, no substitute peptide is used, and the predicted chromatographic retention time is based on the HI of the unlabeled peptide corresponding to the isobarically-labeled peptide—not on the HI of any substituted peptide—and the chromatographic conditions for the targeted analysis. To further accommodate potentially different chromatographic conditions between the labeled and unlabeled experiments, reference peptides (e.g., PRTC) can be employed as retention time landmarks to refine predicted retention times for disparate gradients.

Additional predictive power of the chromatographic retention times for the corresponding unlabeled peptides can be obtained by relation to experimentally-acquired chromatographic retention times of reference peptides. The reference peptides can be, but are not limited to, at least one peptide of a peptide retention time calibration (PRTC) mixtures. The PRTC mixture contains fifteen synthetic heavy peptides mixed at an equimolar ratio that elute across the chromatographic gradient. The observed retention times and hydrophobicity index for these reference peptides may be used to refine the predicted retention times of the unlabeled targeted peptides especially if different chromatography conditions such as column and gradient length are employed.

Targeted quantitation experiments may be performed on a variety of mass spectrometer instruments such as, but not limited to, a triple quadrupole, linear ion trap, Orbitrap, or time-of-flight mass spectrometers, using data acquisition techniques which may include Single Ion Monitoring (SIM), Selected Reaction Monitoring (SRM), Parallel Reaction Monitoring (PRM), synchronous precursor selection (SPS), or any such multiplexed MS$^n$ quantitation technique.

FIG. 5 shows the data for generating an inclusion list, beginning with the quantitative results of TMT-labeled peptides of interest 40, including m/z values, charge state, and experimentally observed retention times, to a list of corresponding predicted properties 50. A comparison between the predicted 50 and experimental 55 results shows that the methods of the present invention provide highly accurate retention time values to enable label-free targeted quantitation. The results of the TMT discovery quantitation experiment in Proteome Discoverer or similar software furnish the requisite information for generation of an inclusion list including but not limited to the peptide sequence, parent m/z value, and charge state(s). Together with the adjusted retention time values from the methods described above and optionally supplemented with information on charge state obtained from a global publically available database containing nearly all human peptides, a complete inclusion list is automatically produced.

Prior to commencing a PRM, MRM, or SIM type experiment the inclusion list comprising at a minimum the m/z value and charge state, but also often the retention type of targeted peptides, must be supplied to the mass spectrometer. Scheduling acquisition according to the peptide's retention time enables the quantitation of significantly more targets. The instrument specific inclusion list is automatically generated by the methods of the present invention. For MRM based quantitation, the inclusion list must also include fragment information, and an additional verification step may be required to determine peptide specific transitions, as the fragmentation pattern can be label specific.

The advantages of the present invention include the use of isobarically labeled multiplexed discovery quantitation as a template to build a method for routine and highly sensitive targeted quantitation without the need for additional intensive validation steps or complex libraries containing fragmentation data. Not only are the methods described herein instrument independent, but the present invention also allows for the use of varied chromatography as isobaric labelling is typically run on longer gradients (e.g. 4 hours) while typical label-free targeted experiments use far shorter gradients (e.g. 60 minutes). The present invention also affords the power to adjust for these disparate gradient lengths and or the use of fractionation allowing easy and effective translation from multiplexed discovery quantitation to routine label-free targeted quantitation.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A data processing system for generating an inclusion list for targeted mass spectrometric analysis, comprising:
   one or more network storage devices configured for receiving experimentally-acquired data for a plurality of isobarically-labeled peptides, the data including, for each one of the isobarically-labeled peptides, a mass-to-charge ratio (m/z), a charge state, and a chromatographic retention time, wherein each of the isobarically-labeled peptides is derived by proteolytic digestion of a corresponding protein;
   one or more processors configured to perform, for each one of the isobarically-labeled peptides, the steps of:
   determining a hydrophobicity index (HI) of an unlabeled peptide corresponding to the isobarically-labeled peptide;
   comparing the determined HI to a threshold value;

if the determined HI is less than the threshold value, selecting a substitute unlabeled peptide in accordance with predetermined criteria, the substitute unlabeled peptide being derivable by proteolytic digestion of the protein from which the isobarically-labeled peptide is derived, determining and storing on the inclusion list predicted properties for the substitute unlabeled peptide, the predicted properties including a predicted m/z, a predicted charge state, and a predicted chromatographic retention time, wherein the predicted chromatographic retention time is based on an HI of the substitute unlabeled peptide and chromatographic conditions for the targeted analysis; and if the determined HI for the unlabeled peptide is at least as great as the threshold value, determining and storing on the inclusion list predicted properties for the unlabeled peptide, the predicted properties including a predicted m/z, a predicted charge state, and a predicted chromatographic retention time, wherein the predicted chromatographic retention time is based on the determined HI of the unlabeled peptide and chromatographic conditions for the targeted analysis.

2. The data processing system of claim 1, wherein the predetermined criteria include the substitute unlabeled peptide having an HI greater than at least 2.0% ACN at LC gradient initial conditions.

3. The data processing system of claim 1, wherein the threshold value of the unlabeled HI is 1.0% ACN at LC gradient initial conditions.

4. The data processing system of claim 2, wherein the substitute unlabeled peptide is selected from an available peptide library of known HI values.

5. The data processing system of claim 1, wherein the proteolytic digestion comprises tryptic digestion.

6. The data processing system of claim 1, wherein the predicted properties further include a predicted fragment ion m/z.

7. The data processing system of claim 1, wherein the experimentally-acquired data further include an amino acid sequence of each of the peptides.

8. The data processing system of claim 1, wherein the predicted chromatographic retention time for the corresponding unlabeled peptide is determined further based on its relation to an experimentally-acquired chromatographic retention time of a reference peptide.

9. The data processing system of claim 8, wherein the reference peptide is at least one peptide of a peptide retention time calibration (PRTC) mixture.

10. The data processing system of claim 1, wherein the isobarically-labeled peptides are tandem mass tag (TMT)-labeled peptides, isobaric tags for relative and absolute quantitation (iTRAQ)-labeled peptides, Combinatorial Isobaric Mass Tags (CMTs), or N,N-Dimethylated Leucine (DiLeu) isobaric tags.

11. The data processing system of claim 1, wherein the mass spectrometric analysis comprises an MS" quantitation step.

12. The data processing system of claim 11, wherein the MS" quantitation step comprises single ion monitoring (SIM), parallel reaction monitoring (PRM), selected reaction monitoring (SRM), synchronous precursor selection (SPS), or $MS^3$ quantitation.

13. The data processing system of claim 1, wherein the hydrophobicity index of the corresponding unlabeled peptide is calculated using a retention time prediction tool.

14. The data processing system of claim 13, wherein the retention time prediction tool is SSRCalc.

15. A method of using a data processing system for generating an inclusion list for targeted mass spectrometric analysis, the method comprising:

receiving experimentally-acquired data for a plurality of isobarically-labeled peptides of interest, the data including, for each one of the isobarically-labeled peptides, a mass-to-charge ratio (m/z), a charge state, and a chromatographic retention time, wherein each of the isobarically-labeled peptides is derived by proteolytic digestion of a corresponding protein;

for each one of the isobarically-labeled peptides, performing steps, via the data processing system, of:

determining a hydrophobicity index (HI) of an unlabeled peptide corresponding to the isobarically-labeled peptide;

comparing the determined HI to a threshold value;

if the determined HI is less than a threshold value, selecting a substitute unlabeled peptide in accordance with predetermined criteria, the substitute unlabeled peptide being derivable by proteolytic digestion of the protein from which the isobarically-labeled peptide is derived, determining and storing on the inclusion list predicted properties for the substitute unlabeled peptide, the predicted properties including a predicted m/z, a predicted charge state, a predicted fragment ion m/z, and a predicted chromatographic retention time, wherein the predicted chromatographic retention time is based on an HI of the substitute unlabeled peptide, chromatographic conditions for the targeted analysis, and on its relation to an experimentally- acquired chromatographic retention time of a reference peptide; and if the determined HI for the unlabeled peptide is at least as great as the threshold value, determining and storing on the inclusion list predicted properties for the unlabeled peptide, the predicted properties including a predicted m/z, a predicted charge state, a predicted fragment m/z, and predicted chromatographic retention time, wherein the predicted chromatographic retention time is based on the determined HI of the unlabeled peptide, chromatographic conditions for the targeted analysis, and on its relation to an experimentally-acquired chromatographic retention time of a reference peptide.

16. The method of claim 15, wherein the predetermined criteria include the substitute unlabeled peptide having an HI of greater than at least 2.0% ACN at LC gradient initial conditions.

17. The method of claim 15, wherein the threshold value of the unlabeled HI is 1.0% ACN at LC gradient initial conditions.

18. The method of claim 16, wherein the substitute unlabeled peptide is selected from an available peptide library of known HI values.

19. The method of claim 15, wherein the reference peptide is at least one peptide of a peptide retention time calibration (PRTC) mixture.

20. The method of claim 15, wherein the hydrophobicity index of the corresponding unlabeled peptide is calculated using a retention time prediction tool.

21. The method of claim 20, wherein the retention time prediction tool is SSRCalc.

* * * * *